(12) United States Patent
Sekiya et al.

(10) Patent No.: US 6,403,846 B1
(45) Date of Patent: Jun. 11, 2002

(54) FLUORINATED, SATURATED HYDROCARBONS

(75) Inventors: Akira Sekiya, Ibaraki; Toshirou Yamada, Kangawa; Takashi Uruma; Tatsuya Sugimoto, both of Kanagawa, all of (JP)

(73) Assignees: Japan as Represented by Director General of Agency of Industrial Science and Technology; Nippon Zeon Co., Ltd., both of Tokyo (JP)

( * ) Notice: Subject to any disclaimer, the term of this patent is extended or adjusted under 35 U.S.C. 154(b) by 0 days.

(21) Appl. No.: 09/423,747
(22) PCT Filed: May 15, 1998
(86) PCT No.: PCT/JP98/02157
§ 371 (c)(1),
(2), (4) Date: Feb. 3, 2000
(87) PCT Pub. No.: WO98/51650
PCT Pub. Date: Nov. 19, 1998

(30) Foreign Application Priority Data

May 15, 1997 (JP) ............................................... 9-125906

(51) Int. Cl.$^7$ .......................... C07C 19/08; C07C 17/00
(52) U.S. Cl. ...................... 570/134; 570/175; 570/176; 570/186
(58) Field of Search ................................. 570/134, 175, 570/176, 186

(56) References Cited

U.S. PATENT DOCUMENTS 4,954,666 A * 9/1990 Bielefeldt et al.
5,171,902 A * 12/1992 Krespan et al.

OTHER PUBLICATIONS

Abstract of JP 5302098 (Nov. 16, 1993).
Abstract of WO 9206941 (Apr. 30, 1992).
Abstract of JP 4025598 (Jan. 29, 1992).
Abstract of JP 6041589 (Feb. 15, 1994).
Abstract of JP 5331490 (Dec. 14, 1993).
Abstract of JP 5331489 (Dec. 14, 1993).

* cited by examiner

Primary Examiner—Sreeni Padmanabhan
Assistant Examiner—Sikarl A. Witherspoon
(74) Attorney, Agent, or Firm—Wenderoth, Lind & Ponack, L.L.P.

(57) ABSTRACT

A composition containing less than 95 mol % of a trihydrofluorinated saturated hydrocarbon represented by the following formula (I)

$$Rf_1-R_1-Rf_2 \qquad (I)$$

(wherein $R_1$ represents a carbon chain in which CHF and $CH_2$ are bound, and $Rf_1$ and $Rf_2$ are bound to each other to form a ring by a perfluoroalkylene chain of 2 to 4 carbon atoms) and the balance of a tetrahydrofluorinated saturated hydrocarbon having the same carbon number and the same carbon structure as the trihydrofluorinated saturated hydrocarbon, as represented by the following formula (II)

$$Rf_1-R_2-Rf_2 \qquad (II)$$

(wherein $R_2$ represents a carbon chain in which $CH_2$ and $CH_3$ are bound, and $Rf_1$ and $Rf_2$ are as defined above) is provided as a composition containing, in a high proportion, trihydrofluorocarbon, a hydrofluorocarbon (HFC) known to have a small global heating coefficient, which has less influence on the global environment, shows less toxicity to animals, and is chemically stable.

21 Claims, No Drawings

FLUORINATED, SATURATED HYDROCARBONS

This application is a 371 application of PCT/JP98/02157 filed May 15, 1998.

1. Technical Field

The invention of this application relates to fluorinated saturated hydrocarbons. More specifically, the invention of this application relates to fluorinated saturated hydrocarbons, which are useful as substitute compounds of CFC (chlorofluorocarbon), HCFC (hydrochlorofluorocarbon), PFC (perfluoro compound), and chlorine-type solvents, which have been widely used as detergents, foaming agents, refrigerants, and the like. The compounds described in the invention of this application have less influence on the global environment, show less toxicity to human bodies, and are chemically stable. The invention of this application also relates to a process for producing the above compounds, and compositions thereof.

2. Background of the Invention

As an industrial method for washing various materials, products composed mainly of CFC 113 or 1,1,1-trichloroethane which are incombustible, low in toxicity, and excellent in stability have been widely used. However, it has been identified that various CFCs, 1,1,1-trichloroethane, carbon tetrachloride and the like destroy the stratospheric ozone layer. In view of the protection of the ozone layer, the production of CFC 113, 1,1,1-trichloroethane and the like has been completely abolished worldwide since the end of 1995, and regulations have been set on their use.

As substitutes of CFC 113 and the like, hydrochlorofluorocarbons such as HCFC 225 and HCFC 141b have been proposed. However, since these compounds are, though slightly, also destructive to the ozone layer, a time limit has been set in their use. Further, chlorinated solvents such as methylene chloride, trichloroethylene, perchloroethylene and the like have also been problematic regarding their safety (carcinogenicity and intoxication), and various regulations have been already set or are being studied.

Further, various fluorine type compounds which do not contain chlorine atoms that cause the destruction of the ozone layer, and can maintain non-combustibility, safety and such merits as mentioned above, have been synthesized. For example, a product composed mainly of perfluorocarbons such as perfluoro-n-heptane (WO 92-03205 and the like), a product composed mainly of acyclic hydrofluorocarbon (WO 95-06693, JP-W-6-501949 and the like), a product composed mainly of specific acyclic hydrofluorocarbons (WO 95-05448) and the like are mentioned.

These perfluorocarbons and hydrofluorocarbons were preferable because there is no worry for the destruction of the ozone layer and detergency with good finish is exhibited by using the same as such or along with organic solvents. However, these compounds each had problems that needed to be improved. For example, perfluorocarbons have high global warming coefficient, and there is fear that new problems on the preservation of the global environment might occur. Further, with respect to acyclic or cyclic hydrofluorocarbons, various structures have been proposed, but have problems in their structures. For example, compounds having —$CH_2CH_2$— bonds, with 4 or 5 carbon atoms, and a boiling point in the region suitable for detergents or solvents, are combustible.

Accordingly, an object of the invention of this application is to provide, upon improving the defects of such hydrofluorocarbons known so far, fluorinated saturated hydrocarbons which are excellent as detergents, and excellent in their non-combustibility and their stability in the presence of water, which can construct now detergents and the like, and are easy to produce, a process for producing the same, and compositions thereof.

DISCLOSURE OF THE INVENTION

The invention of this application is to provide, as a product to solve the above-mentioned problems, a composition comprising less than 95 mol % of a trihydrofluorinated saturated hydrocarbon (A) represented by the following formula (I)

$$Rf_1—R_1—Rf_2 \qquad (I)$$

(wherein $R_1$ represents a carbon chain in which CHF and $CH_2$ are bound, and $Rf_1$ and $Rf_2$ are bound to each other to form a ring by a perfluoroalkylene chain of 2 to 4 carbon atoms)
and the balance of a tetrahydrofluorinated saturated hydrocarbon (B) having the same number of carbons and the same carbon structure as the trihydrofluorinated saturated hydrocarbon (A), as represented by the following formula (II)

$$Rf_1—R_2—Rf_2 \qquad (II)$$

(wherein $R_2$ represents a carbon chain in which $CH_2$ and $CH_2$ are bound, and $Rf_1$ and $Rf_2$ are as defined above).

The reason that the proportions of the fluorinated saturated hydrocarbons (A) and (B) are as mentioned above is that according to the invention of this application, the fluorinated hydrocarbon of this invention is provided by a specific process described later in this application, and as a content of a detergent or the like, the fluorinated saturated hydrocarbon of this invention is introduced as a novel product.

The proportion of the trihydrofluorinated hydrocarbon (A) is less than 95 mol %, generally 10 mol % or more, preferably 50 mol % or more, more preferably 70 mol % or more, further preferably 80 mol % or more. The higher the proportion of the trihydrofluorinated hydrocarbon (A), the more the fluorinated saturated hydrocarbon of this invention becomes non-combustible.

The fluorinated saturated hydrocarbons (A) and (B) are cyclic. The number of carbon atoms in the fluorinated hydrocarbons is between 4 and 6, and most preferably 5. Specific compounds of the fluorinated saturated hydrocarbon (A) having the trihydrofluorocarbon chain include 1,1,2,2,3-pentafluorocyclobutane, 1,1,2,2,3,3,4-heptafluorocyclopentane, and 1,1,2,2,3,3,4,4,5-nonafluorocyclohexane, of which 1,1,2,2,3,3,4-heptafluorocyclopentane (HFCPA) is mentioned as especially preferable.

In this invention, the tetrahydrofluorinated saturated hydrocarbon (B) having the same number of carbons and the same carbon structure as the trihydrofluorinated saturated hydrocarbon (A) co-exists. For example, it is shown that 1,1,2,2,3,3-hexafluorocyclopentane co-exists with 1,1,2,2,3,3,4-heptafluorocyclopentane (HFCPA) mentioned above.

The composition of this invention is excellent in detergency, is highly non-combustible, is excellent in stability under the presence of water, and the production thereof is easy.

Thus, the process for producing the composition of the invention of this application is described.

The process for producing the composition of this invention, which contains the fluorinated hydrocarbon compounds represented by formulas (III) and (IV) such as the fluorinated hydrocarbons (A) and (B) mentioned above, is quite unique. For example, the formation of 1H,1H,2H-heptafluorocyclopentane or the like which is a trihydro compound has been so far observed during the reaction of hydrogenating perfluorocyclopentene in the presence of palladium-alumina, and it is disclosed that the main product of this reaction is 1H,2H-octafluorocyclopentane (J. Chem. Soc., C.548 (1968)). Only 10% of heptafluorocyclopentane (HFCPA) having a trihydrofluorocarbon chain was reportedly obtained, and further, was difficult to separate from octafluorocyclopentane (OFCPA) by distillation.

Moreover, according to the official gazette of JP-B-5-148171, when 1,1,1,2,2,3,4,5,5,5-decafluoropentane is produced by hydrogenating decafluoropentene-2 using palladium supported on carbon, alumina, or the like as a catalyst, by products such as 1,1,1,2,2,4,5,5,5-nonafluoropentane, 1,1,1,2,2,3,5,5,5-nonafluoropentane, 1,1,1,2,2,5,5,5-octafluoropentane and the like were produced in large amounts. However, it was reportedly difficult to separate these by-products from the desired product by the process of distillation.

That is, providing fluorinated saturated hydrocarbons containing heptafluorocyclopentane (HFCPA) and the like which contain trihydrofluorocarbon chains in high proportions has not been industrially realized so far.

Meanwhile, in the process of this invention, a cyclic fluorinated, unsaturated hydrocarbon having the unsaturated fluorocarbon chain as represented by formula (V) is used as a substrate starting material, and is catalytically reduced in a hydrogen atmosphere using a noble metal catalyst. Here, the proportions of the fluorinated saturated hydrocarbon of formula (III) and the fluorinated saturated hydrocarbon of formula (IV) are controlled by changing the polarity of the component in the reaction system, other than the substrate starting material.

That is, in the method of this invention, the fluorinated saturated hydrocarbon of formula (III) can be produced more selectively by making the polarity of the component other than the substrate starting material of the reaction system high. On the other hand, the fluorinated saturated hydrocarbon of formula (IV) can be produced more selectively by making the polarity of the component other than the substrate starting material of the reaction system low. For example, when an unsaturated fluorinated hydrocarbon having carbon chains of —CF=CF—, as in formula (V), is the starting material, where the symbol X represents a fluorine atom (F), a trihydrofluorinated saturated hydrocarbon having a carbon chain of —CHF—CH$_2$— as the fluorinated saturated hydrocarbon of formula (III) can be produced by making the polarity of the component other than the substrate starting material of the reaction system high. Meanwhile, when an unsaturated, fluorinated hydrocarbon having a carbon chain of —CH=CF— in which the symbol X in formula (V) represents a hydrogen atom (H) is used as a starting material, a trihydrofluorinated saturated hydrocarbon having a carbon chain of —CHF—CH$_2$— as the fluorinated saturated hydrocarbon of formula (IV) can selectively be produced by making the polarity of the component other than the substrate starting material of the reaction system low.

In the fluorinated, unsaturated hydrocarbon represented by formula (V) as the substrate starting material, the carbon number is between 4 and 6, most preferably 5. Further, the fluorinated, unsaturated hydrocarbon is cyclic. The starting material can be obtained depending on various methods and the like. For example, the synthesis thereof can be conducted by a method described in the official gazette of JP-A-8-12608 or the like.

Here, the component other than the substrate starting material of the reaction system refers to high-polarity compounds or low-polarity compounds added to the substrate starting material, or impurities accompanying the substrate starting material.

That is, in order to make the polarity of the component other than the substrate starting material of the reaction system high, it is advisable to use, for example, a starting material containing the fluorinated, unsaturated hydrocarbon represented by formula (V) as the substrate starting material, and a high-polarity compound or a starting material obtained by removing the low-polarity compounds from the impurities accompanying the substrate starting material to increase the proportion of the high-polarity compounds in impurities. Further, in order to make the polarity of the component other than the substrate starting material of the reaction system low, it is advisable to use, for example, a starting material containing the fluorinated, unsaturated hydrocarbon represented by formula (V) and a low-polarity compound or a starting material obtained by removing the high-polarity compounds from impurities accompanying the substrate starting material to increase the proportion of the low-polarity compound in impurities. Here, the polarity of the compound used can be defined by a dielectric constant as described in, for example, Organic Solvents (John A. Riddick, et al (1986), John Wiley & Sons, Inc. 4th Edition), Kagaku Binran (Kisohen II, II-498 to II-501) or the like.

Accordingly, a process in which a trihydrofluorinated saturated hydrocarbon in which the symbol X of formula (III) represents a fluorine atom, is selectively produced by making the polarity of the component other than the substrate starting material of the reaction system high, is first described.

In this case, a compound in which the symbol X in formula (V) represents a fluorine atom is used as a starting material. Specific examples thereof include, for example, cyclic fluorinated, unsaturated hydrocarbons such as 1,1,2,2,3,4-hexafluorocyclobutene, 1,1,2,2,3,3,4,5-octafluorocyclopentene, 1,1,2,2,3,3,4,4,5,6-decafluorocyclohexene and the like; and so forth. Of these, 1,1,2,2,3,3,4,5-octafluorocyclopentene is mentioned especially preferably.

The low-polarity compound of which the amount has to be adjusted to a small amount relative to the substrate, in order to make the polarity of the component other than the substrate starting material of the reaction system high includes, for example, paraffins such as n-pentane, n-hexane, n-heptane, n-octane, n-nonane, n-decane, n-undecane, n-dodecane, n-tridecane, n-tetradecane, n-pentadecane and the like, and structural isomers thereof; naphthenes such as cyclopentane, cyclohexane, methylcyclohexane and the like; aromatics such as benzene, toluene, o-xylene, m-xylone, p-xylene and the like, and analogues thereof; mineral oils such as a machine oil, a cutting oil, a printing ink oil, a vacuum pump oil and the like; chlorofluorocarbons such as chlorononafluorocyclopentane, chloroheptafluorocyclopentene and the like; and so forth. The content of these low-polarity compounds is 1% by weight or less, preferably 0.5% by weight or less, more preferably 0.1% by weight or less.

The low-polarity compound to be noted especially is paraffins, naphthenes and aromatics.

The low-polarity compound accompanying the substrate starting material can reduce the content in the starting material by means such as adsorption treatment using an adsorbent and the like. For example, the treatment with an adsorbent such as an activated carbon or the like is a typical one.

And in the process of this invention, it is also important that the substrate starting material is mixed with the high-polarity compound. As the high-polarity compound, there are water, alcohols, polyhydric alcohols, monoethers of these polyhydric alcohols, amides, sulfoxides and the like. Specific examples include, for example, alcohols such as methyl alcohol, ethyl alcohol, n-propyl alcohol, n-butyl alcohol, n-pentyl alcohol and the like, and their structural isomers; polyhydric alcohols such as ethylene glycol, glycerol, diethylene glycol, diethylene glycol monomethyl ether and the like, and monoethers of these polyhydric alcohols; amides such as N,N-dimethylacetamide, N,N-dimethylformamide and the like; sulfoxides such as dimethyl sulfoxide and the like; and so forth. The mixing proportion of these high-polarity compounds is not particularly limited, and they may be used as additives or solvents. Further, these high-polarity compounds may be used either alone or in mixtures of two or more.

Usually, the mixing proportion is between 0.1 and 20% by weight based on the substrate starting material. It is preferably between 0.1 and 15% by weight, more preferably between 0.5 and 15% by weight.

Next, a process for producing the fluorinated saturated hydrocarbon of formula (IV) more selectively by making the polarity of the component other than the substrate starting material of the reaction system low is described.

In this case, it is important that the low-polarity compound is contained in the starting material. Examples of the low-polarity compound are the same as the above-mentioned. It is advisable that the proportion of these low-polarity compounds is between 0.1 and 20% by weight. It is preferably between 0.1 and 15% by weight, more preferably between 0.5 and 15% by weight. Further, these low-polarity compounds may be used either alone or in admixture of two or more.

Further, in this invention, it is also important to reduce the content of the high-polarity impurities relative to the starting material. Examples of the high-polarity compound are the same as the above-mentioned. The content of these high-polarity impurities has to be 1% by weight or less in the starting material. It is preferably 0.5% by weight or less, more preferably 0.1% by weight or less.

With respect to the high-polarity compound accompanying the substrate starting material, the content in the starting material can be decreased by means such as adsorption treatment using an adsorbent or the like. For example, treatment with an adsorbent such as activated alumina or the like is a typical one.

The trihydrofluorinated saturated hydrocarbon in which the symbol X in formula represents a hydrogen atom is selectively produced as the fluorinated saturated hydrocarbon of formula (IV) by making low the component other than the substrate starting material of the reaction system. In this case, the starting material is a compound represented by the formula (V), in which X is a hydrogen atom. Examples include cyclic fluorinated, unsaturated hydrocarbons such as 1,1,2,2,3-pentafluorocyclobutene, 1,1,2,2,3,3,4-heptafluorocyclopentene and the like. Of these, 1,1,2,2,3,3,4-heptafluorocyclopentene is mentioned especially preferably.

The fluorinated saturated hydrocarbon containing the trihydrofluorinated hydrocarbon (A) and the tetrahydrofluorinated saturated hydrocarbon (B) in this invention corresponds to the case in which the fluorinated unsaturated hydrocarbon of the following formula where the symbol X represents a hydrogen atom, is used as the starting compound of formula (V), as mentioned above.

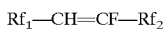

The trihydrofluorinated saturated hydrocarbon (A) can be controlled to a proportion of less than 95 mol % while co-existing with the tetrahydrofluorinated saturated hydrocarbon (B).

As the noble metal catalyst in the process of this invention, a noble metal supported on a carrier is usually used. The noble metal mentioned here refer to palladium, rhodium, ruthenium, rhenium and platinum. Palladium, rhodium and ruthenium are most preferable. These metals may be used either alone or as an alloy of two or more metals, a so-called bimetal catalyst. The type, shape and size of the carrier are not particularly limited. Activated carbon, alumina and titania are preferable. They may be powders, or molded products such as spheres and pellets. The amount of the noble metal supported on the carrier is between 0.5 and 20% by weight. It is recommendable that the amount supported is between 1 and 20% by weight in powder and between 1 and 10% by weight in molded products. More preferably, a catalyst powder having the amount supported of from 1 to 10% by weight is recommended.

The reaction pressure is not particularly limited. A pressure in the range of atmospheric pressure to 10 kgf/cm$^2$ is recommended. The reaction temperature is not particularly limited, either. A temperature in the range of ordinary temperature to 350° C. is recommended. Further, the reaction, may be conducted in a liquid phase, or a gaseous phase, as required.

After the completion of the reaction, as a post-treatment, purification may be conducted by filtering the catalyst, neutralizing and washing the resulting filtrate and conducting distillation. For example, when octafluorocyclopentene (OFCPE) is hydrogenated by the process of this invention, hexafluorocyclopentane can be formed. The boiling point of this compound is between 87 and 88° C. at atmospheric pressure, while the boiling point of heptafluorocyclopentane (HFCPA) is 80° C. at atmospheric pressure, and the boiling point of octafluorocyclopentane (OFCPA) is 79° C. at atmospheric pressure. Accordingly, they can easily be separated through distillation.

When the fluorinated saturated hydrocarbons (A) and (B) are used in a solvent composition constituting a detergent, the proportion of the fluorinated saturated hydrocarbon (A) having the trihydrofluorocarbon chain usually exceeds 10%, and is preferably 50% by weight or more, more preferably 70% or more, most preferably 80% or more. This is because as the proportion of the trihydrofluorinated saturated hydrocarbon (A) is increased, the non-combustibility of the fluorinated saturated hydrocarbon increase.

In case of constituting the composition, it is effective to contain at least one organic solvent having a boiling point of at least 25° C. and at most 250° C. to increase the solubility of contaminants such as oils, flux, waxes and the like. The amount of these organic solvents added is not particularly limited, but is usually 50% by weight or less, preferably between 2 and 30% by weight, more preferably between 3 and 20% by weight based on the total amount. When the organic solvent forms an azeotropic composition, use in the region of the azeotropic composition is preferable.

The type of such an organic solvent is not particularly limited. For example, at least one organic solvent selected from hydrocarbons, alcohols, esters, chlorinated hydrocarbons, other fluorinated hydrocarbons, others, ketones and volatile organic silicones may be used.

The hydrocarbons mentioned above, are not particularly limited. For example, aliphatic hydrocarbons such as n-pentane, n-hexane, n-heptane, isohexane, isoheptane, n-octane, isooctane, n-decane, isodecane, n-undecane, n-dodecane, n-tridecane and the like, alicyclic hydrocarbons such as cyclopentane, methylcyclopentane, cyclohexane, methylcyclohexane and the like, and aromatic hydrocarbons such as benzene, toluene, xylene and the like can be selected.

The alcohols mentioned above are not particularly limited either. For example, methanol, ethanol, isopropanol, n-propanol, n-butanol, s-butanol, t-butanol, n-pentanol, isopentanol, n-hexanol, isohexanol, 2-ethylhexanol, n-octanol and the like are mentioned. Of these, those having 5 or less carbon atoms are preferable, and those having 1 to 4 carbon atoms are especially preferable.

The esters mentioned above are not particularly limited either. For example, methyl acetate, ethyl acetate, propyl acetate, isopropyl acetate, butyl acetate, isobutyl acetate, pentyl acetate, methyl propionate, ethyl propionate, propyl propionate, isopropyl propionate, methyl butyrate, ethyl butyrate, isopropyl butyrate, methyl valerate, ethyl valerate and the like are mentioned. Of these, those having 3 to 10 carbon atoms are preferable, and those having 3 to 6 carbon atoms are especially preferable.

The chlorinated hydrocarbons mentioned above are not particularly limited. For example, methylene chloride, dichloroethane, dichloroethylene, trichloroethylene, perchloroethylene and the like are mentioned.

The fluorinated hydrocarbons mentioned above are not particularly limited, and may be mainly composed of carbon, hydrogen and fluorine and contain oxygen atoms or unsaturated bonds. Of these, those having boiling points of 25° C. or more are preferable. As such fluorinated hydrocarbons, for example, pentafluoropropane, hexafluorobutane, decafluoropentane, hexafluorocyclopentane, octafluorocyclopentane, perfluoropropylmethyl ether, perfluorobutylmethyl ether, perfluorobutylethyl ether, hexafluorocyclopentane, heptafluorocyclopentane, octafluorocyclopentene and the like can be used. Further, hexafluorocyclopentane, octafluorocyclopentane, hexafluorocyclopentene and the like having cyclic structures and the appropriate boiling points are preferable.

The ketones mentioned above are not particularly limited. For example, acetone, 2-butanone, 2-pentanone, 3-pentanone, 2-hexanone, 3-methyl-2-butanone, cyclopentanone, cyclohexanone, 2-methyloyclopentanone, 2-methylcyclohexanone and the like may be selected.

As the volatile organosilicones mentioned above, hexamethyldisiloxane, octamethyltrisiloxane, decamethyltetrasiloxane, hexamethylcyclotrisiloxane, octamethylcyclotetrasiloxane, decamethylcyclopentasiloxane and the like are mentioned.

Further, various additives known so far may be added to the detergent of this invention. As additives, there are, for example, stabilizers, surfactants and the like. As the stabilizer, aliphatic nitro compounds such as nitromethane, nitroethane and the like, acetylene alcohols such as 3-methyl-1-butyn-3-ol, 3-methyl-1-pentyn-3-ol and the like, epoxides such as glycidol, methylglycidyl ether, acrylglycidyl ether and the like, ethers such as dimethoxymethane, 1,4-dioxane and the like, unsaturated hydrocarbons such as hexene, heptene, cyclopentene, cyclohexene and the like, unsaturated alcohols such as allyl alcohol, 1-buten-3-ol and the like, acrylates such as methyl acrylate, ethyl acrylate and the like, and so forth are mentioned.

Further, as the surfactant, anionic surfactants, cationic surfactants, nonionic surfactants, and amphoteric surfactants known so far may be used. As the anionic surfactant, for example, a carboxylate, a sulfonate, a sulfate, a phosphate and the like may be used. As the cationic surfactant, for example, salts of amines and various acids and quaternary ammonium salts are mentioned. As the nonionic surfactant, for example, polyoxyethylene ether, polyoxyethylene-polyoxypropylene glycol, polyoxyethylone-polyoxypropylene alkyl ether, polyhydric alcohol aliphatic acid partial ester and the like are mentioned. As the amphoteric surfactant, for example, betaines, organic amino acids, amine salts of fatty acids and the like are mentioned. Further, surfactants containing fluorine atoms are also preferable. When these surfactants are added, it is possible to effectively remove and dry the water adhered to processed parts of metals, ceramics, glasses, plastics, elastomers and the like, after water-washing. The amount of the surfactant is not particularly limited. It is usually 30% by weight or less, preferably 20% by weight or less, more preferably between 0.005 and 10% by weight based on the total amount.

The products to be washed are not particularly limited either. For example, metals, ceramics, glasses, plastics, elastomers and the like used in industries such as the precision machinery industry, the metal processing industry, the optical machinery industry, the electronic industry, and plastics industry may be washed with the product of this invention. Specifically, a wide variety of products such as automobile parts, as in bumpers, gears, mission parts, and radiator parts, electronic and electric parts such as printed circuit boards, IC parts, lead frames, motor parts, and condensers, precision machine parts such as bearings, gears, engineering plastics gears, watch parts, camera parts, optical lenses and such, large-sized machine parts such as printers, printer blades, printing rolls, flat rolled products, building machines, glass substrates, and large-sized heavy machine parts, household products such as tableware, and fiber products may be mentioned as examples.

The types of the contaminants, removed by product of the present invention, may be oils such as cutting oils, quenching oils, rolling oils, lubricants, machine oils, press oils, blanking oils, drawing oils, assembling oils, and wire drawing oils, as well as greases, waxes, adhesives, fats and oils, release agents in molding, thumb-marks, flux after soldering, resists, and solder pastes.

With respect to the washing method, the product to be washed may be washed by its contact with the washing solvent composition, using regular washing methods. Specifically, methods such as hand wiping, dipping, spraying, showering or the like may be applied. In these treatments, physical means such as ultrasonic vibration, shaking, stirring, brushing or the like may be used in combination.

In the washing process, an organic solvent made of at least one type selected from aliphatic hydrocarbons, alicyclic hydrocarbons, aromatic hydrocarbons, alcohols, esters, chlorinated hydrocarbons, ethers, ketones and volatile organosilicones may also be used as a solvent other than the detergent of the present invention.

In such a case, a method comprising two steps, a step of removing contaminants of the product to be washed and a step of rinsing an organic solvent adhered to the product after the removal of contaminants by contacting the same with the detergent of this invention or vapor-cleaning the same in a vapor of a detergent (so-called co-solvent system), is employed.

On the basis of the foregoing, preferred modes for carrying out this invention are summed up below.

1. The number of carbon atoms in the trihydrofluorinated saturated hydrocarbon (A) is 5.

2. The trihydrofluorinated saturated hydrocarbon is 1,1,2,2,3,3,4-heptafluorocyclopentane.
3. The fluorinated saturated hydrocarbon of formula (III) is selevtively produced through catalytic reduction by making the component other than the substrate starting material of the reaction system to have a high polarity.
4. In the above-mentioned 3, the catalytic reduction is conductd using a starting material in which the proportion of the high-polarity compound in the impurities is increased by adding a high-polarity compound in the fluorinated unsaturated hydrocarbon represented by formula (V) used as the substrate starting material, or by removing the low-polarity compound from the impurities accompanying the substrate starting material.
5. The fluorinated saturated hydrocarbon of formula (IV) is selectively produced through catalytic reduction by making the component other than the substrate starting material of the reaction system have a low polarity.
6. In the above-mentioned 5, the catalytic reduction is conducted using a starting material in which the proportion of the low-polarity compound in the impurities is increased by adding a low-polarity compound in the fluorinated unsaturated hydrocarbon represented by formula (V) used as the substrate starting material, or by removing the high-polarity compound from the impurities in the substrate starting material.
7. In the above-mentioned 4, the low-polarity compound is added to the starting material in an amount of 0.5% by weight or less.
8. In the above-mentioned 4, the high-polarity compound is contained in the starting material in an amount of 0.1 to 15% by weight.
9. In the above-mentioned 6, the high-polarity compound is added to the starting material in an amount of 0.5% by weight.
10. In the above-mentioned 6, the low-polarity compound is added to the starting material in an amount of 0.1 to 15% by weight.
11. In the above-mentioned 4 or 6, the low-polarity compound is a paraffin, napthene or aromatic compound.
12. In the above-mentioned 4 or 6, the high-polarity compound is an alcohol, a polyhydric alcohol, a polyhydric alcohol monoether, an amide, or a sulfoxide.
13. In the above-mentioned 4, the low-polarity compound accompanying the substrate starting material reduces the content in the starting material by adsorption treatment with an absorbent.
14. In the above-mentioned 6, the high-polarity compound accompanying the substrate starting material reduces the content in the starting material by adsorption treatment with an adsorbent.
15. In the above-mentioned 3, a trihydrofluorinated saturated hydrocarbon of formula (III) is selectively produced by using a fluorinated unsaturated hydrocarbon having carbon chains of —CF=CF— as in formula (V) as the starting material, in which the symbol X represents a fluorine atom.
16. In the above-mentioned 5, a trihydrofluorinated saturated hydrocarbon of formula (IV) is selectively produced by using a fluorinated, unsaturated hydrocarbon having a carbon chain of —CH=CF— as in formula (V) as the starting material, in which the symbol X represents a hydrogen atom.
17. The fluorinated, unsaturated hydrocarbon of formula (V) as the starting material in the above-mentioned 3 or 5 has 5 carbon atoms.
18. The fluorinated, unsaturated hydrocarbon used as the starting material in the abve-mentioned 15 is 1,1,2,2,3,3,4,5-octafluorocyclopentene.
19. The fluorinated, unsaturated hydrocarbon used as the starting material in the above-mentioned 16 is 1,1,2,2,3,3,4-heptafluorocyclopentene.
20. In the above-mentioned 3 or 5, the catalytic reduction is conducted under hydrogen in the presence of a noble metal catalyst.
21. In the above-mentioned 20, the noble metal is palladium, rhodium, ruthenium, rhenium or platinum.
22. In the above-mentioned 21, the noble metal is palladium, rhodium or ruthenium.
23. In the above-mentioned 20, the noble metal catalyst is one in which the noble metal is contained in a carrier.
24. In the above-mentioned 23, the carrier is activated carbon, alumina or titania.
25. In the above-mentioned 23, the amount of metal contained in the carrier is between 0.5 and 20% by weight.
26. In the above-mentioned 20, the catalytic reduction is conducted as a liquid phase reaction or a gaseous phase reaction at a pressure in the range of atmospheric pressure to 10 kg/cm$^2$, in a hydrogen atmosphere, and a temperature in the range of ordinary temperature to 350° C.
27. In a composition containing the fluorinated saturated hydrocarbons (A) and (B), the proportion of the trihydrofluorinated saturated hydrocarbon (A) exceeds 10 mol %.
28. In the above-mentioned 27, it is 50 mol % or more.
29. In the above-mentioned 28, it is 70 mol % or more.
30. In the above-mentioned 29, it is 80 mol % or more.
31. In the above-mentioned 27, an organic solvent having a boiling point of at least 25° C. and at most 250° C., is 50% or less by weight of the total amount.
32. In the above-mentioned 31, it is between 2 and 30% by weight.
33. In the above-mentioned 32, it is between 3 and 20% by weight.
34. In the above-mentioned 31, the organic solvent is a hydrocarbon, an alcohol, an ester, a chlorinated hydrocarbon, a fluorinated hydrocarbon, an ether, a ketone or a volatile organosilicone.

The mode for carrying out this invention is illustrated more specifically by referring to the following Examples.

EXAMPLE 1

One percent by weight of n-tridecane (dielectric constant 2.0), a low-polarity compound, was dissolved in crude 1,3,3,4,4,5,5-heptafluorocyclopentene having a purity of 99.9 GC %. An autoclave having a capacity of 100 ml was charged with a catalyst of activated carbon having supported thereon 5% by weight of powdered palladium. After the deaeration under reduced pressure, n-tridecane-containing 1,3,3,4,4,5,5-heptafluorocyclopentene prepared previously was poured. While the mixture was stirred at 40° C., the reaction was conducted by repeating block charge of hydrogen at a gauge pressure in the range of 0 to 6 kgf/cm$^2$. After the completion of the reaction, the product was analyzed through gas chromatography. Consequently, a fluorinated saturated hydrocarbon containing 94 mol % of 1,1,2,2,3,3,4-heptafluorocyclopentane (HFCPA) and 6 mol % of 1,1,2,2,3,3-hexafluorocyclopentane was obtained.

EXAMPLE 2

The reaction was conducted as in the above-mentioned Example 1 without adding n-tridecane. Consequently, a product containing 70 mol % of 1,1,2,2,3,3,4-heptafluorocyclopentane and 30 mol % of 1,1,2,2,3,3-hexafluorocyclopentane was obtained.

EXAMPLE 3

Activated carbon as a typical nonionic adsorbent was charged into crude octafluorocyclopentene containing low-polarity hydrocarbon impurities and having a purity of 99 GC %. These were stirred, and filtered to remove the low-polarity compound from the impurities of the crude starting material. Octafluorocyclopentene having a purity of 99.9 GC % in which the proportion of the high-polarity compound in the impurity was increased was obtained. Then, an autoclave having a capacity of 100 ml was charged with a catalyst of activated carbon having supported thereon 5% by weight of palladium powder. After the deaeration under reduced pressure, octafluorocyclopentene (dielectric constant: 2.6) having a purity of 99.9% as prepared previously was poured in. While the mixture was stirred at 40° C., the reaction was conducted by repeating block charge of hydrogen at a gauge pressure in the range of 0 to 6 kgf/cm². After the completion of the reaction, the product was analyzed through gas chromatography. Consequently, a fluorinated saturated hydrocarbon containing 75 mol % of heptafluorocyclopentane (HFCPA) and 25 mol % of octafluorocyclopentane (OFCPA) was obtained.

EXAMPLE 4

Crude octafluorocyclopentene having a purity of 99 GC % was mixed with the same volume of diethylene glycol monomethyl ether as a high-polarity compound. An autoclave having a capacity of 100 ml was charged with a catalyst of activated carbon having supported thereon 5% by weight of palladium powder. After the deaeration under reduced pressure, the mixture of octafluorocyclopentene and diethylene glycol monomethyl ether prepared previously was poured. While the resulting mixture was stirred at 40° C., the reaction was conducted by repeating block charge of hydrogen at a gauge pressure in the range of 0 to 6 kgf/cm². After the completion of the reaction, the product was analyzed through gas chromatography. Consequently, a fluorinated saturated hydrocarbon containing 85 mol % of heptafluorocyclopentane (HFCPA) and 15 mol % of octafluorocyclopentane (OFCPA) was obtained.

EXAMPLE 5

One percent by weight of n-tridecane (dielectric constant 2.0), a low-polarity compound, was dissolved in crude octafluorocyclopentene having a purity of 99.9 GC %. An autoclave having a capacity of 100 ml was charged with a catalyst of activated carbon containing 5% by weight of palladium powder. After deaeration under reduced pressure,—tridecane-containing octafluorocyclopentene prepared previously was poured in. While the mixture was stirred at 40° C., the reaction was conducted by repeating the block charge of hydrogen at a gauge pressure in the range of 0 to 6 kgf/cm². The product obtained was analyzed through gas chromatography. Consequently, a fluorinated saturated hydrocarbon containing 83 mol % of octafluorocyclopentane (OFCPA) and 17 mol % of heptafluorocyclopentane (HFCPA) was obtained.

EXAMPLE 6 n-Tridecane (3% by weight), a low-polarity compound was dissolved in crude octafluorocyclopentene having a purity of 99.9 GC %. An autoclave having a capacity of 100 ml was charged with a catalyst of activated carbon having supported thereon 5% by weight of palladium powder. After the deaeration under reduced pressure, n-tridecane-containing octafluorocyclopentene prepared previously was poured in. While the mixture was stirred at 40° C., the reaction was conducted by repeating block charge of hydrogen at a gauge pressure in the range of 0 to 6 kgf/cm². After the completion of the reaction, the product was analyzed through gas chromatography. Consequently, a fluorinated saturated hydrocarbon containing 86 mol % of octafluorocyclopentane (OFCPA) and 14 mol % of heptafluorocyclopentane (HFCPA) was obtained.

EXAMPLE 7

One percent by weight of o-xylene (dielectric constant 2.6), a low-polarity compound was dissolved in crude octafluorocyclopentene having a purity of 99.9 GC %. An autoclave having a capacity of 100 ml was charged with a catalyst of activated carbon having containing 5% by weight of palladium powder. After the deaeration under reduced pressure, o-xylene-containing octafluorocyclopentene prepared previously was poured. While the mixture was stirred at 40° C., the reaction was conducted by repeating block charge of hydrogen at a gauge pressure in the range of 0 to 6 kgf/cm². After the completion of the reaction, the product was analyzed through gas chromatography. Consequently, a fluorinated saturated hydrocarbon containing 87 mol % of octafluorocyclopentane (OFCPA) and 13 mol % of heptafluorocyclopentane (HFCPA) was obtained.

EXAMPLE 8

Activated alumina as a typical ionic adsorbent was charged into crude octafluorocyclopentene having a purity of 99 GC %. These were stirred, and filtered to remove the high-polarity impurity from the impurities of the crude starting material. Octafluorocyclopentene having a purity of 99.5 GC % in which the proportion of the low-polarity compound, in the impurities was increased, was obtained. An autoclave having a capacity of 100 ml was charged with a catalyst of activated carbon having supported thereon 5% by weight of palladium as a powder. After the deaeration under reduced pressure, octafluorocyclopentene having a purity of 99.5% as obtained previously was poured. While the mixture was stirred at 40° C., the reaction was conducted by repeating block charge of hydrogen at a gauge pressure in the range of 0 to 6 kgf/cm². After the completion of the reaction, the product was analyzed through gas chromatography. Consequently, a fluorinated saturated hydrocarbon containing 74 mol % of octafluorocyclopentane (OFCPA) and 26 mol % of heptafluorocyclopentane (HFCPA) was obtained.

EXAMPLE 9

A flux (PO-F-1010S made by Senju Metal Industry Co., Ltd.) was coated on the whole surface of a printed substrate (30 mm×30 mm×0.2 mm in thickness) made of a polyimide resin, and dried at room temperature. This was dipped in a detergent composition of 80 parts by weight of a fluorinated saturated hydrocarbon of heptafluorocyclopentane: hexafluorocyclopentane=0:40 (molar ratio) and 20 parts by weight of ethanol at 30° C. for 3 minutes. The condition of removing the flux was visually observed. Consequently, it was identified that the flux was completely removed.

EXAMPLE 10

A product obtained by aligning 50 press-molded parts (made of stainless steel, 50 mm square) and bundling the same with a wire was prepared. This was dipped in a beaker containing a press oil (Tafuny Punch Oil made by Idemitsu Kosan Co., Ltd.) at room temperature, and an ultrasonic wave was applied for 1 minute to coat the press oil throughout the product. The product was allowed to stand as such in the solution for 30 minutes, and was then withdrawn from the press oil. The product was allowed to stand for 5 minutes for removal of the oil. This sample was dipped in a fluorinated saturated hydrocarbon of heptafluorocyclopentane: hexafluorocyclopentane=80:20 (molar ratio) at 50° C. for 3 minutes while applying an ultrasonic wave, and further steam-washed in the steam of the same fluorinated saturated hydrocarbon as mentioned above. After cooling, the removal of the oil was visually observed, and the odor was confirmed. Consequently, it was identified that the oil was completely removed.

EXAMPLE 11

A test for drying by draining was conducted using the same fluorinated saturated hydrocarbon as in Example 1.

A cover glass (15 mm×15 mm) was previously washed by degreasing. This was dipped as a test piece in pure water, and then in 100 ml of the composition in Example 1 for 30 seconds. The test piece was withdrawn, and allowed to stand at room temperature for 1 minute for the evaporation of the residual composition.

Subsequently, it was placed in 10 g of ethanol (water content 570 ppm), and the water content increased of ethanol was measured with a Karl Fischer's water content meter. Consequently, it was 30 ppm.

The increase in water content for a blank was measured using a cover glass which was allowed to stand at room temperature. Consequently, it was 50 ppm.

Further, the increase in water content of a product which was dipped in pure water alone and not in the composition was 3,200 ppm.

In view of the foregoing, it was found that drying by draining could be conducted almost completely by using the composition of this Example.

Industrial Applicability

The invention of this application has made it possible, for the first time, to provide a hydrofluorocarbon (HFC), which have been known to cause no damage in the ozone layer, and to have a small global heating coefficient, especially a fluorinated saturated hydrocarbon containing high proportions of trihydrofluorocarbon, which is excellent in its chemical stability and its safety towards animals. Consequently, a fluorinated saturated hydrocarbon containing, in a high proportion, trihydrofluorocarbon which can safely be used as a substitute compound of CFC (chlorofluorocarbon) or HCFC (hydrochlorofluorocarbon) that has found so far wide acceptance as detergents, drain-drying agents, foaming agents, refrigerants and the like, can widely be supplied on the market.

And it goes without saying that the fluorinated hydrocarbon of the invention of this application can be used as a detergent, a rinse detergent, a vapor-cleaning detergent, a gap detergent or a drain-drying detergent.

Further, with respect to the other specific use, there are, for example, various test solvents such as solvents for testing the voltage resistance of a switch, solvents for testing ceramics polarization, solvents for testing the voltage resistance of a cathode ray tube socket, solvent for testing the voltage resistance of a film condenser and the like; liquid mediums for rectifiers; liquid mediums for transformers; liquid mediums for condensers; cooling heating liquid mediums for cooling in semiconductor production or cooling of a dry etching device, cooling of ozone devices, cooling of liquid crystal projectors, cooling of power supply heat exchangers or the like; solvents for the production of a fluoropolymers; solvents for film formation with a fluorine/silicone polymer; detergents for hollow fibers; dry cleaning solvents; solvent of a fluorine-containing electrolytes; solvents for forming surface lubricant layer of magnetic disks or magnetic tapes; solvent for checking cracks or leak of castings, ceramics product or the like; chemical reaction solvents in a reaction using a Lewis acid catalyst or the like; blow washing solvents; solvents for polishing disks ouch as a silicon wafer substrate, metallic substrate, glass substrate or the like; detergents for production of conductor IC chips; solvent for surface treatment of a printed circuit board; solvent for chemical mechanical polishing; photoresist solvents; developer solvents; rinse compositions; and so forth. It can also be used as medical mediums. For example, there are aerosol solvents for human bodies containing agents such as anti-inflammatory agents, muscular fatigue treating agents, local warming agents, analgesic or antipruritic agents, blood circulation accelerators, external agents of formulation for coating or spraying onto the human skin, inhalants, collunariums, deodorants, disinfectants, clean wiping agents or the like; mediums for air sterilization; detergents for the sterilization of dialysis hollow fibers; mediums for cryoperation using a catheters or cooling a medical cooler of the head or the like; polymer-containing liquids for forming polymer films on surfaces of disposal products such as catheters, insert units, guide wires, circuits, sensors and the like, and embedding products such as artificial blood vessels, stents, an artificial bones and the like; detergents of disposal products such as catheters, insert units, guide wires, injection needles, circuits, bags, sensors and the like, embedding products such as artificial blood vessels, stents, artificial bones, dental members and the like, and rigid units such as forcepses, cutters (scissors), tweezers, rib spreaders and the like; pressure mediums for continuously administering small. amounts of drugs to the affected portions; solvents for production of drug-containing gelatin capsules; solvents for coating a lubricants and solvents for removing a lubricants in production of medical catheters; solvents for coating lubricants and solvents for removing lubricants in artificial organs, artificial blood vessels and the like; and so forth.

What is claimed is:

1. A composition comprising less than 95 mol % of a trihydrofluorinated saturated hydrocarbon (A) represented by the following formula (I)

$$Rf_1-R_1-Rf_2 \qquad (I)$$

(wherein $R_1$ represents a carbon chain in which CHF and $CH_2$ are bound, and $Rf_1$ and $Rf_2$ are bound to each other and together represent a perfluoroalkylene chain of 2 to 4 carbon atoms, thus forming a ring with $R_1$)

and the balance of a tetrahydrofluorinated saturated hydrocarbon (B) having the same carbon number and the same carbon structure as said trihydrofluorinated saturated hydrocarbon (A), as represented by the following formula (II)

$$Rf_1-R_2-Rf_2 \qquad (II)$$

(wherein $R_2$ represents a carbon chain in which $CH_2$ and $CH_2$ are bound, and $Rf_1$ and $Rf_2$ are as defined above).

2. The composition of claim 1, wherein the trihydrofluorinated saturated hydrocarbon (A) is an alicyclic, fluorinated hydrocarbon having 5 carbon atoms.

3. The composition of claim 1, wherein the proportion of the trihydrofluorinated saturated hydrocarbon (A) is 10 mol % or more.

4. The composition of claim 1, wherein the proportion of the trihydrofluorinated saturated hydrocarbon (A) is 50 mol % or more.

5. A process for producing a composition comprising a compound represented by the following formula (III)

$$Rf_1-R_1-Rf_2 \qquad (III)$$

(wherein $R_1$ represents a carbon chain in which CHX and $CH_2$ are bound, X represents a hydrogen atom or a fluorine atom, and $Rf_1$ and $Rf_2$ are bound to each other and together represent a perfluoroalkylene chain of 2 to 4 carbon atoms, thus forming a ring with $R_1$)
and a compound represented by the following formula (IV)

$$Rf_1-R_2-Rf_2 \qquad (IV)$$

(wherein $R_2$ represents a carbon chain in which CHX and CHF are bound, and X, $Rf_1$ and $Rf_2$ are as defined above), which consists essentially of catalytically reducing a fluorinated, unsaturated hydrocarbon represented by the following formula (V)

$$Rf_1-R_3-Rf_2 \qquad (V)$$

(wherein $R_3$ represents a carbon chain of $-CX=CF-$, X represents a hydrogen atom or a fluorine atom, and $Rf_1$ and $Rf_2$ are bound to each other and together represent a perfluoroalkylene chain of 2 to 4 carbon atoms, thus forming a ring with $R_1$) under hydrogen using a noble metal catalyst, and controlling the proportions of the fluorinated saturated hydrocarbon of formula (III) and the fluorinated saturated hydrocarbon of formula (IV) by changing the polarity of the component other than the substrate starting material of the reaction system.

6. The process for producing a composition of claim 5, wherein the fluorinated saturated hydrocarbon of formula (III) is selectively produced through catalytic reduction by making the component other than the substrate starting material of the reaction system to have a high polarity.

7. The process for producing a composition of claim 6, wherein the catalytic reduction is conducted using a starting material in which the proportion of the high-polarity compound in impurities is increased by containing the high-polarity compound in the fluorinated, unsaturated hydrocarbon represented by formula (V) as the substrate starting material or by removing a low-polarity compound from among impurities accompanying the substrate starting material.

8. The process for producing a composition of claim 5, wherein the fluorinated saturated hydrocarbon of formula (IV) is selectively produced through catalytic reduction by making the component other than the substrate starting material of the reaction system to have a low polarity.

9. The process for producing a composition of claim 8, wherein the catalytic reduction is conducted using a starting material in which the proportion of the low-polarity compound in impurities is increased by containing the low-polarity compound in the fluorinated, unsaturated hydrocarbon represented by formula (V) as the substrate starting material or by removing the high-polarity compound from among impurities accompanying the substrate starting material.

10. The process for producing a composition of claim 7, wherein the low-polarity compound is contained in the starting material in an amount of 0.5% by weight or less, or the high-polarity compound is contained in the starting material in an amount in the range of 0.1 to 15% by weight.

11. The process for producing a composition of claim 9, wherein the high-polarity compound is contained in the starting material in an amount of 0.5% by weight or less, or the low-polarity compound is contained in the starting material in an amount in the range of 0.1 to 15% by weight.

12. The process for producing a composition of claim 7 or 9, wherein the low-polarity compound is selected from the group consisting of paraffins, naphthenes and aromatics, and the high-polarity compound is selected from the group consisting of alcohols, polyhydric alcohols, polyhydric alcohol monoethers, amides and sulfoxides.

13. The process for producing a composition of claim 6, wherein a trihydrofluorinated saturated hydrocarbon of formula (III) is selectively produced by using a fluorinated, unsaturated hydrocarbon having a carbon chain of $-F=CF-$ in which the symbol X in formula (V) represents a fluorine atom as a starting material.

14. The process for producing a composition of claim 8, wherein a trihydrofluorinated saturated hydrocarbon of formula (IV) is selectively produced by using a fluorinated, unsaturated hydrocarbon having a carbon chain of $-CH=CF-$ in which the symbol X in formula (V) represents a hydrogen atom as a starting material.

15. The process for producing a composition of claim 6 or 8, wherein formula (V) of the starting material is an alicyclic fluorinated, unsaturated hydrocarbon having 5 carbon atoms.

16. The process for producing a composition of claim 5, wherein the noble metal is palladium, rhodium, ruthenium, rhenium or platinum.

17. The process for producing a composition of claim 5, wherein the catalytic reduction is conducted as a liquid phase reaction or a gaseous phase reaction at a temperature in the range of room temperature to 350° C. under hydrogen of a pressure in the range of atmospheric pressure to 10 kg/cm².

18. The composition of any one of claim 1, 2, or 4, further comprising at least one type of an organic solvent having a boiling point of at least 25° C. and at most 250° C.

19. The composition of claim 18, wherein the amount of the organic solvent having the boiling point of at least 25° C. and at most 250° C. is 50% by weight or less based on the total amount.

20. The composition of claim 19, wherein the amount of the organic solvent is between 2 and 30% by weight based on the total amount.

21. The composition of claim 19, wherein the organic solvent is selected from the group consisting of hydrocarbons, alcohols, esters, chlorinated hydrocarbons, fluorinated hydrocarbons, ethers, ketones and volatile organosilicones.

* * * * *